United States Patent [19]
Purwar

[11] Patent Number: 6,066,292
[45] Date of Patent: May 23, 2000

[54] STERILIZATION PROCESS FOR PHARMACEUTICAL SUSPENSIONS

[75] Inventor: Shivaji Purwar, Monroe, Conn.

[73] Assignee: Bayer Corporation, Pittsburgh, Pa.

[21] Appl. No.: 08/994,626

[22] Filed: Dec. 19, 1997

[51] Int. Cl.$^7$ .................................................... A61L 2/04
[52] U.S. Cl. .............................. 422/1; 210/650; 514/171; 552/503; 552/574; 552/576; 552/577; 552/588
[58] Field of Search ................................ 422/1; 514/178, 514/179, 180, 182, 171; 552/503, 577, 574, 588, 576, 566; 210/650

[56] References Cited

U.S. PATENT DOCUMENTS 3,962,430   6/1976   O'Neill ...................................... 514/64
5,536,413   7/1996   Bormann et al. ......................... 210/650

*Primary Examiner*—Elizabeth McKane
*Attorney, Agent, or Firm*—Huw R. Jones

[57] ABSTRACT

The invention is directed to a method for sterilizing a pharmaceutical formulation comprising a suspension of a water-insoluble pharmaceutical, comprising the steps of heat-sterilizing an aqueous solution of a viscosity enhancer, to result in a first sterile pre-mix. Next is sterile-filtering an aqueous solution of a mixture of a pharmaceutically-active compound, which results in a second sterile pre-mix. Next is heat-sterilizing a mixture of water, a water-insoluble pharmaceutical, and at least a partial amount of an electrolyte to provide a sub-saturated solution of the electrolyte, and adding under aseptic conditions an aqueous surfactant, to give a third sterile pre-mix. Finally, combining all three pre-mixes in sterile fashion to achieve a sterile suspended pharmaceutical formulation. Thus, for the third pre-mix, use of either Sodium chloride (in varying proportion) or Sodium acetate (in one proportion, but not limited to) is given as an example. The invention is also directed to methods for making sterile suspensions of pharmaceutically active compositions including Ciprofloxacin and hydrocortisone, and pharmaceutical compositions made according to this process.

30 Claims, 11 Drawing Sheets

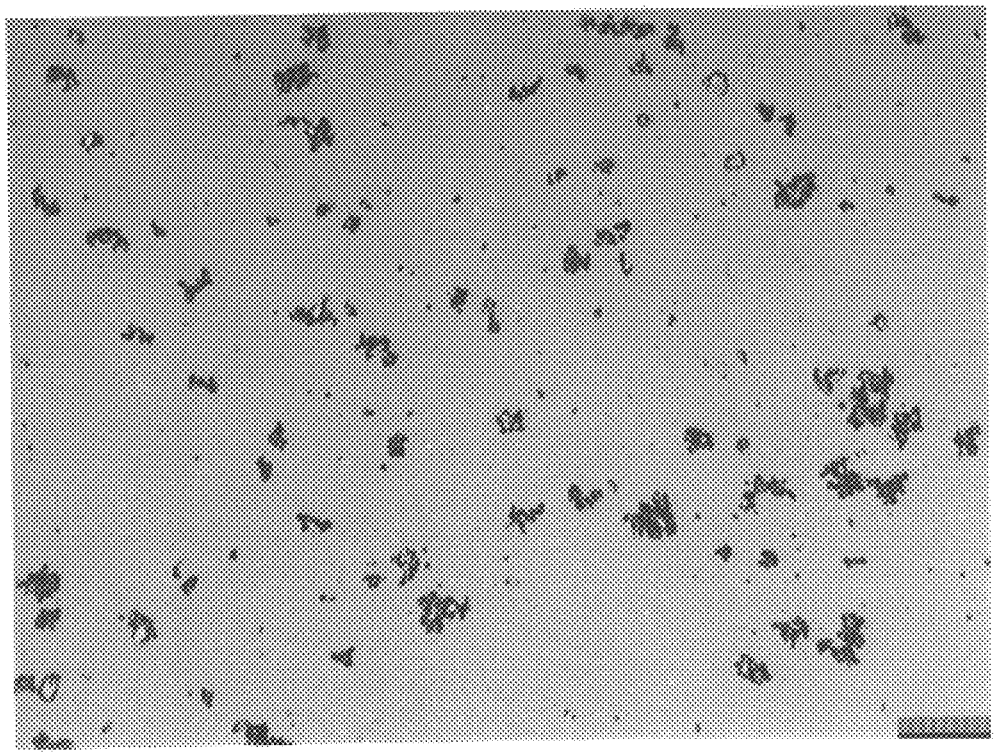
FIG. 8A  10 um
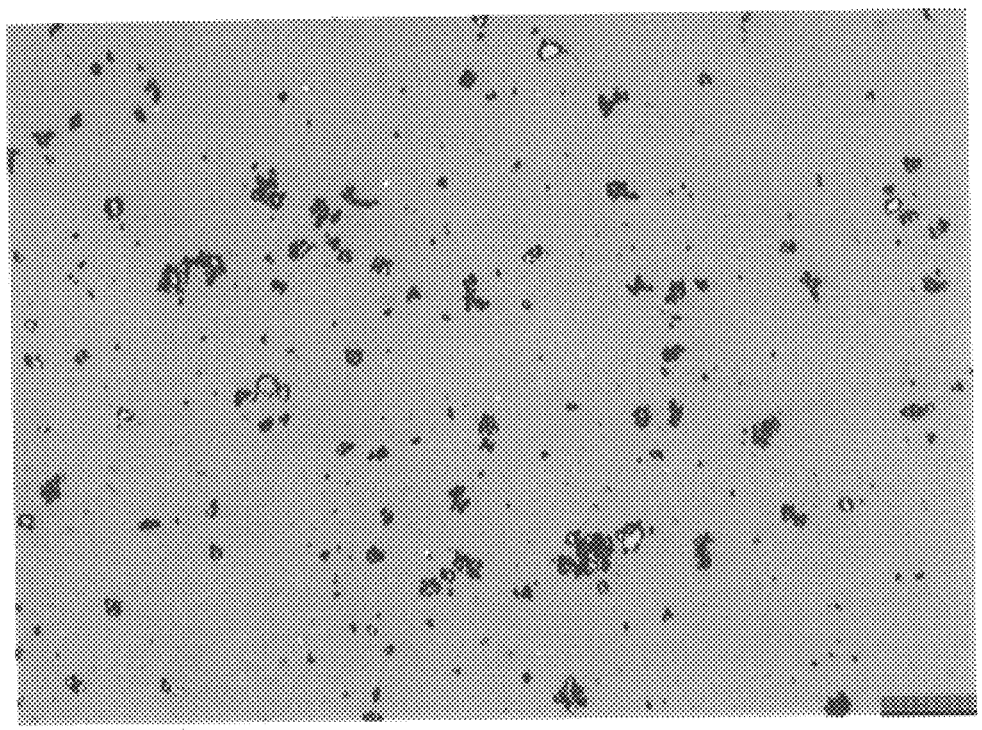
FIG. 8B  10um

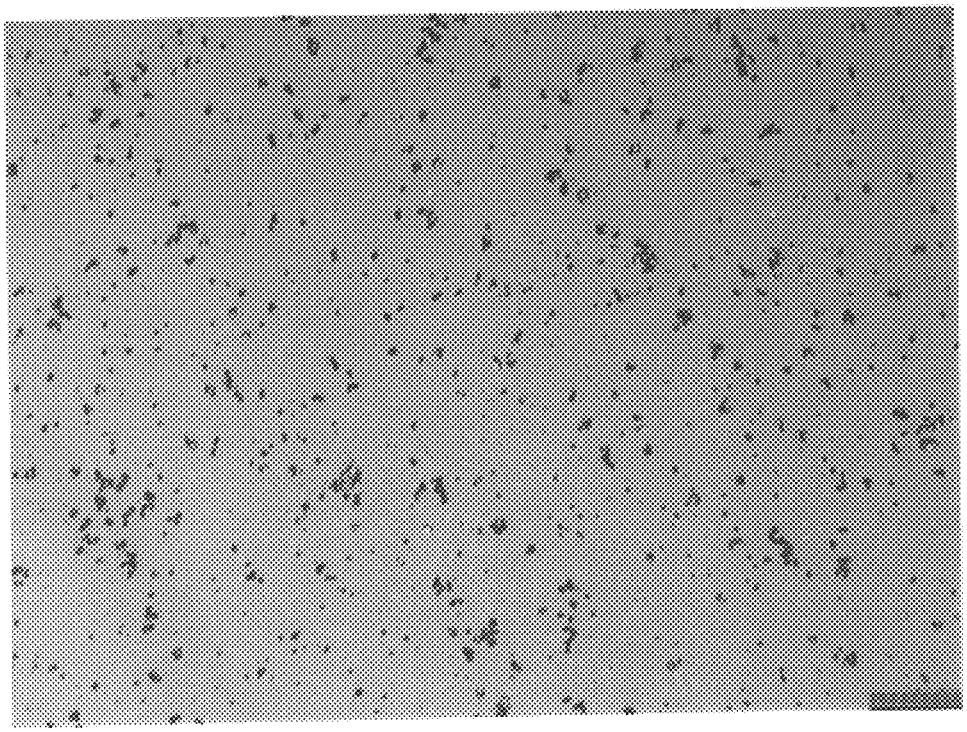
FIG. 9A  10 um
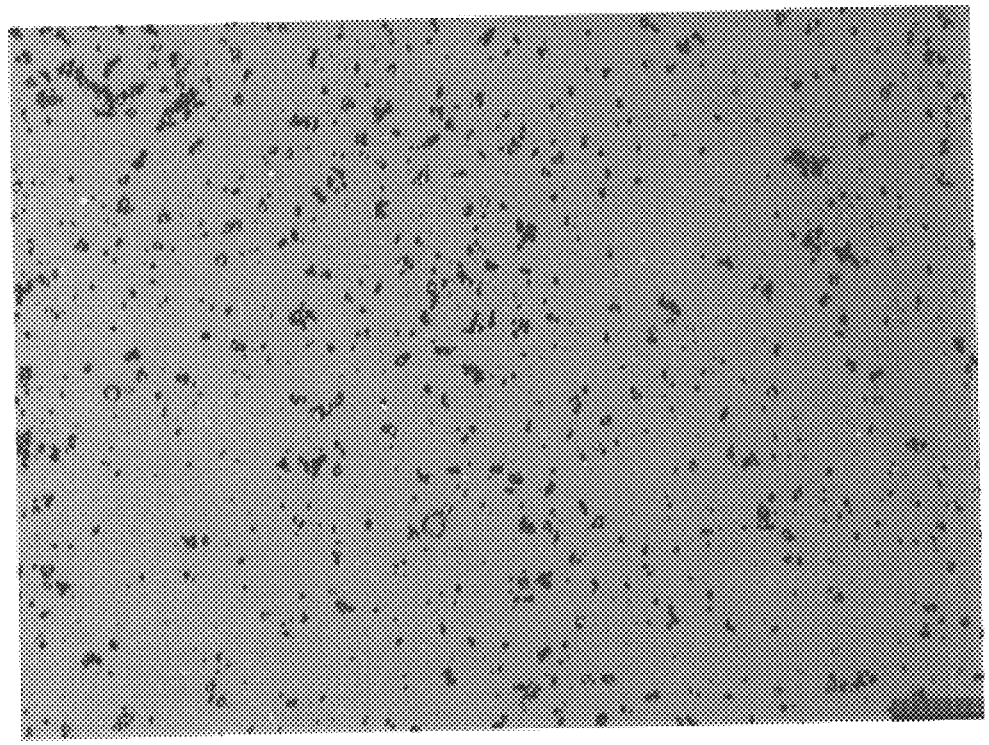
FIG. 9B  10 um

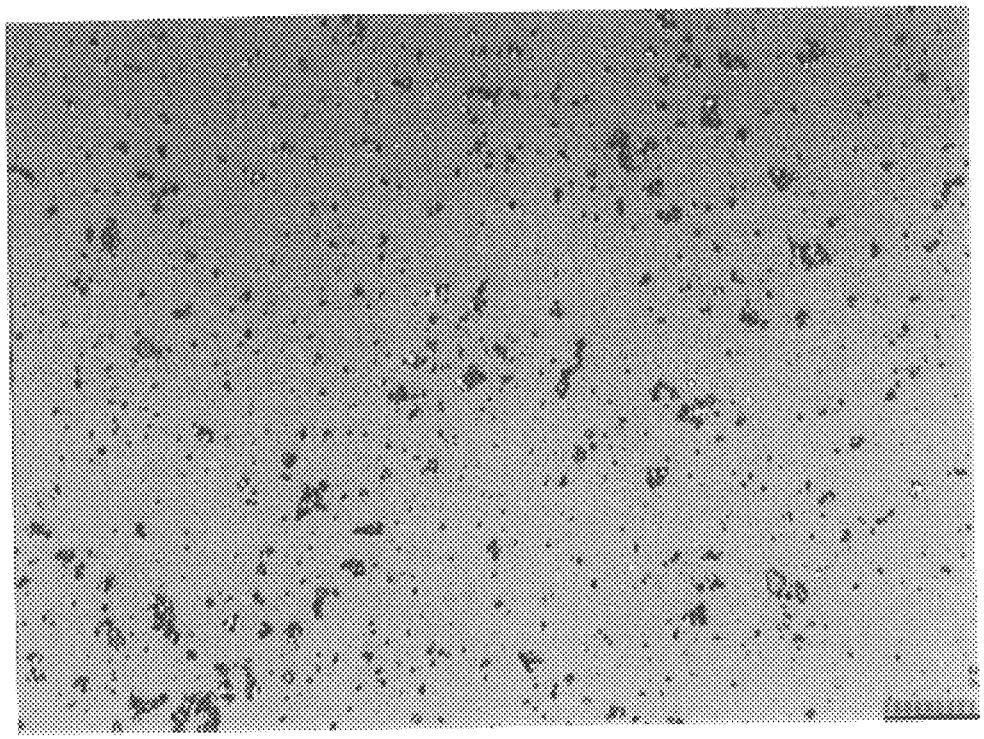
FIG. 10A  10 um
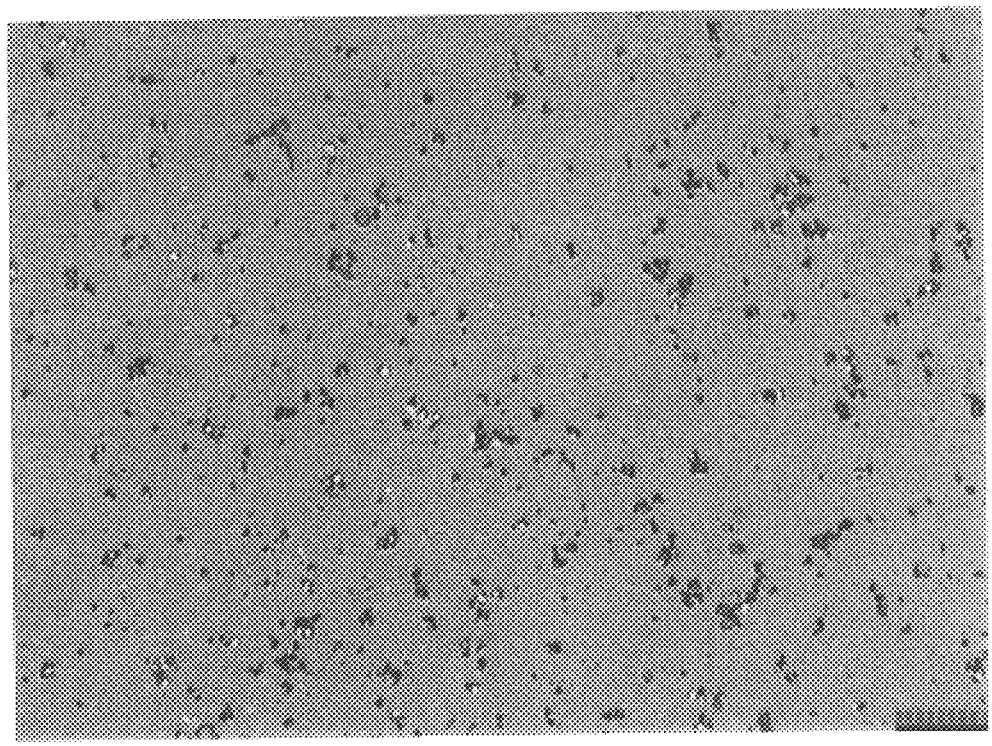
FIG. 10B  10 um

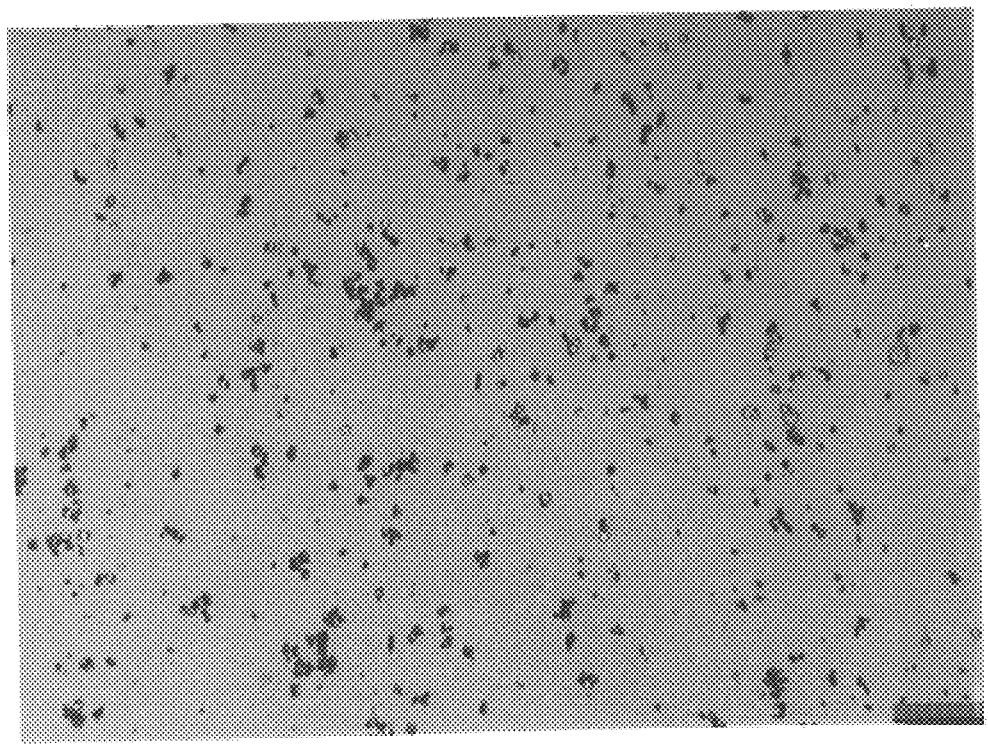
FIG. 11A  10 um
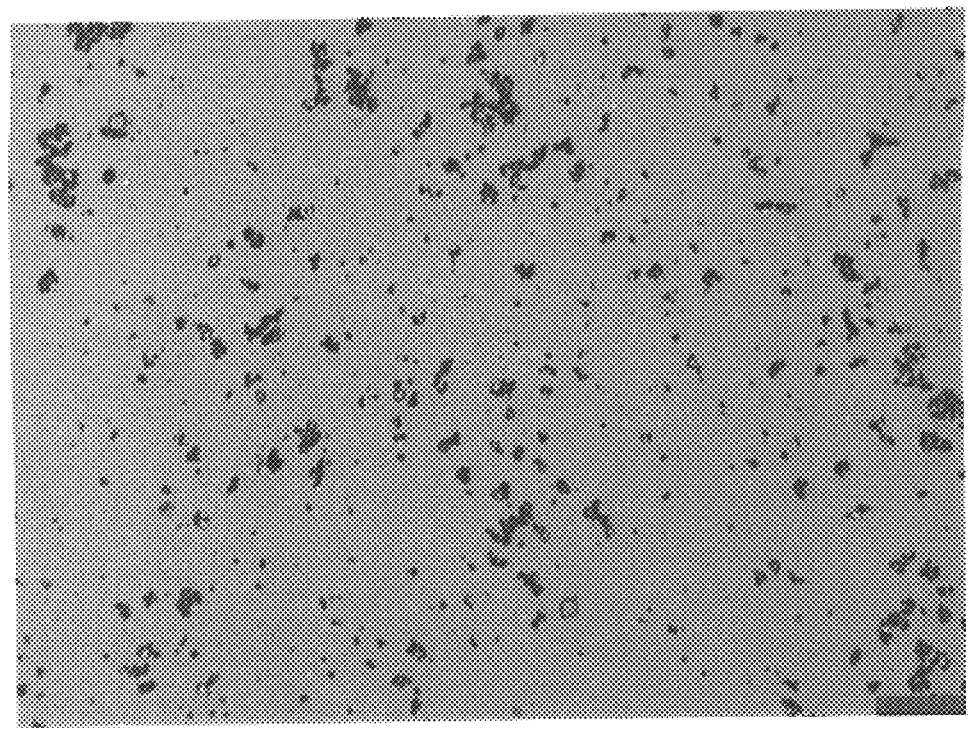
FIG. 11B  10 um

STERILIZATION PROCESS FOR PHARMACEUTICAL SUSPENSIONS

BACKGROUND

1. Field of the Invention

The invention is generally related to the art of pharmaceutical manufacturing and methods of production. Specifically, it is related to processes of sterilizing a pharmaceutical composition comprising a suspension of an insoluble component in an aqueous phase while maintaining the redispersibility, homogeneity, uniformity and particle particle size of the suspension.

2. Description of Related Art

The need for sterility in certain pharmaceutical formulations is mandated both by concerns for the general public's safety, and a pharmaceutical company's reputation for producing quality products. Formulations intended for the ears in general ("otic") and eyes in particular ("opthalmic") are mandated by the FDA to be sterile, even though after the first access to what is intended to be a multi-use package, they will lose their sterility for subsequent uses.

To produce a sterile pharmaceutical suspension product is technically a challenging task. Today it is common to use the following five techniques and/or chemicals for sterilizing any given pharmaceutical suspension product: wet steam (autoclaving), dry heat, aseptic filtration, ethylene oxide, and irradiation.

All of the present methods have deficiencies or limitations. The first two methods involve a high degree of heat, and only chemically thermostable materials or products can be sterilized by these methods. Additionally, in the case of a suspension product, heat also impacts unfavorably on the physical attributes of the suspension by altering flocculation, sedimentation, and redispersion characteristics of the suspended particles. In many cases heat affects the homogeneity or uniformity of the final product either by catalyzing the formation of loose agglomerations called "curds," or, if the curds become compacted and fuse, "cakes" of suspended particles. Curds and cakes negatively impact on the patient or caregiver's ability to re-suspend the product easily and provide uniform dosing.

The aseptic filtration technique cannot be utilized for suspension products due to non-filterability of suspended particles, which requires passing the product through a 0.22 $\mu$m filter, and is suited only for solution products with low to moderate viscosity which can be filtered through such a fine filter.

The ethylene oxide method has been a widely used method for suspension products where product or components are thermolabile. Most of the currently marketed suspension products utilize this technique where individual components are sterilized by this method and then processed or assembled together aseptically. The technique, however, requires the elimination of residual ethylene oxide from the product which is a time consuming and difficult process with still some ethylene oxide left. Most of the products sterilized by this method were introduced in the market decades ago, and probably would not be allowed to be introduced today due to present day's stringent regulatory requirement for almost zero ethylene oxide residue.

Finally, the radiation technique causes immense analytical difficulties due to its possible degradative impact on the pharmaceutical components, and therefore is avoided in the industry. Only packaging components, or containers etc. are sterilized by this method. Safety for human exposure is also a concern.

Procedures for sterilizing suspensions include ethylene oxide exposure, and the wet steam method in combination with saturated sodium chloride, cited below in U.S. Pat. No. 3,962,430. As previously mentioned, the ethylene oxide method is being phased out, and so new methods are sought to sterilize suspensions. The main problem to be overcome in heating a suspension is the likelihood that the suspended material will dissolve in the aqueous solution at the high temperature necessary for sterilization, and then as the suspension cools it may recrystallize in different crystal form, shape and size than the original particles. This recrystallization and/or other thermal effects disrupts the overall homogeneity characteristics of the suspension, which are critical to good manufacturing practice and reliability of dispensing the suspension product. This is because suspensions which tend to settle out over time may form hard "cakes" which do not redisperse upon shaking.

U.S. Pat. No. 3,962,430 (O'Neil) is directed to a method of sterilization of insoluble non-electrolyte medicinal agents by heating in a aqueous suspension which contains saturated sodium chloride. Corticosteroids are given by example as the solid non-electrolyte medical agents, including as shown in Example 11, Hydrocortisone. The method shown depends upon the use of an over-saturated solution of NaCl, as discussed in column 2, lines 27–33. Solutions having less than saturated NaCl have significant drawbacks, including re-crystallization, as discussed in column 3, lines 51–61. The re-suspendability characteristics of the suspensions are not discussed.

Other patents disclose in a more general fashion aqueous suspensions of sparingly soluble pharmaceuticals, including U.S. Pat. No. 5,599,824 (Grunenberg et al.), U.S. Pat. No. 4,150,150 (Straub) and U.S. Pat. No. 4,892,741 (Ohm et al.).

There exists a need for more flexible methods of sterilizing suspensions having one or more water insoluble components.

SUMMARY OF THE INVENTION

The present invention overcomes the shortcomings of the prior art need for a saturated solution of sodium chloride. A sterilization process using the wet steam method has been developed herein to sterilize two-component suspensions where one of the components is largely water insoluble, retaining the preferable physical and chemical attributes of the non-sterile product. A particular aspect of the invention has been utilized to produce the Ciprofloxacin®-Hydrocortisone otic suspension product. The key step in the process, steam sterilization of hydrocortisone-the main suspended particle component, involves a carefully balanced minimum quantity of water and use of an electrolyte in the hydrocortisone slurry to avoid solubilization during heating and subsequent recrystallization of hydrocortisone on cooling. This is important in order to retain the original particle size and particle size distribution of the micronized hydrocortisone.

The invention is directed to a method for sterilizing a pharmaceutical formulation comprising a suspension of a water-insoluble pharmaceutical, comprising the steps of first heat-sterilizing an aqueous solution of a viscosity enhancer, to result in a first sterile pre-mix. Next is sterile-filtering an aqueous solution of a mixture of a pharmaceutically-active compound, which results in a second sterile pre-mix. Next is heat-sterilizing a mixture of water, a water-insoluble pharmaceutical, and at least a partial amount of an electrolyte to provide a sub-saturated solution of the electrolyte, and adding under aseptic conditions an aqueous surfactant, to give a third sterile pre-mix. Finally, combining all three pre-mixes in sterile fashion to achieve a sterile suspended pharmaceutical formulation. Thus, for the third pre-mix use of either Sodium chloride (in varying proportion) or Sodium acetate (in one proportion, but not limited to) is given as an example.

Another embodiment of the invention is directed to a method for sterilizing a pharmaceutical suspension of a water-insoluble pharmaceutical, comprising the steps of first heat-sterilizing an aqueous solution of a viscosity enhancer, to give a first sterile pre-mix. Next is sterile-filtering an aqueous solution of a pharmaceutically-active compound, and at least a partial amount of an electrolyte to give a second sterile pre-mix. The next step is heat-sterilizing a mixture of water, a micronized water-insoluble pharmaceutical, and at least a partial amount of said electrolyte using less than a saturated solution of said electrolyte, and adding under aseptic conditions an aqueous surfactant, to give a third sterile pre-mix. The next step is optimizing resuspendability of the suspension by balancing the amounts of electrolyte between said second and third sterile pre-mixes so that the total amount of said electrolyte is the total formula amount of the batch formulation. Finally, combining all three pre-mixes in sterile fashion thereby achieving a sterile suspended pharmaceutical formulation.

The invention is also directed to a pharmaceutical suspension of a water-insoluble pharmaceutical with a pharmaceutically active component made by the above-recited process. A particularly preferred combination is Ciprofloxacin® and Hydrocortisone.

BRIEF DESCRIPTION OF THE DRAWINGS

FIGS. 8–11 show the before and after photomicrographs (100×) of non-sterile (top) and sterilized (bottom) suspension samples. FIG. 8 is Hydrocortisone acetate; FIG. 9 is Dexamethasone; FIG. 10 is Dexamethasone acetate; FIG. 11 is Prednisone.

DESCRIPTION OF THE PREFERRED EMBODIMENTS

Figure 1:
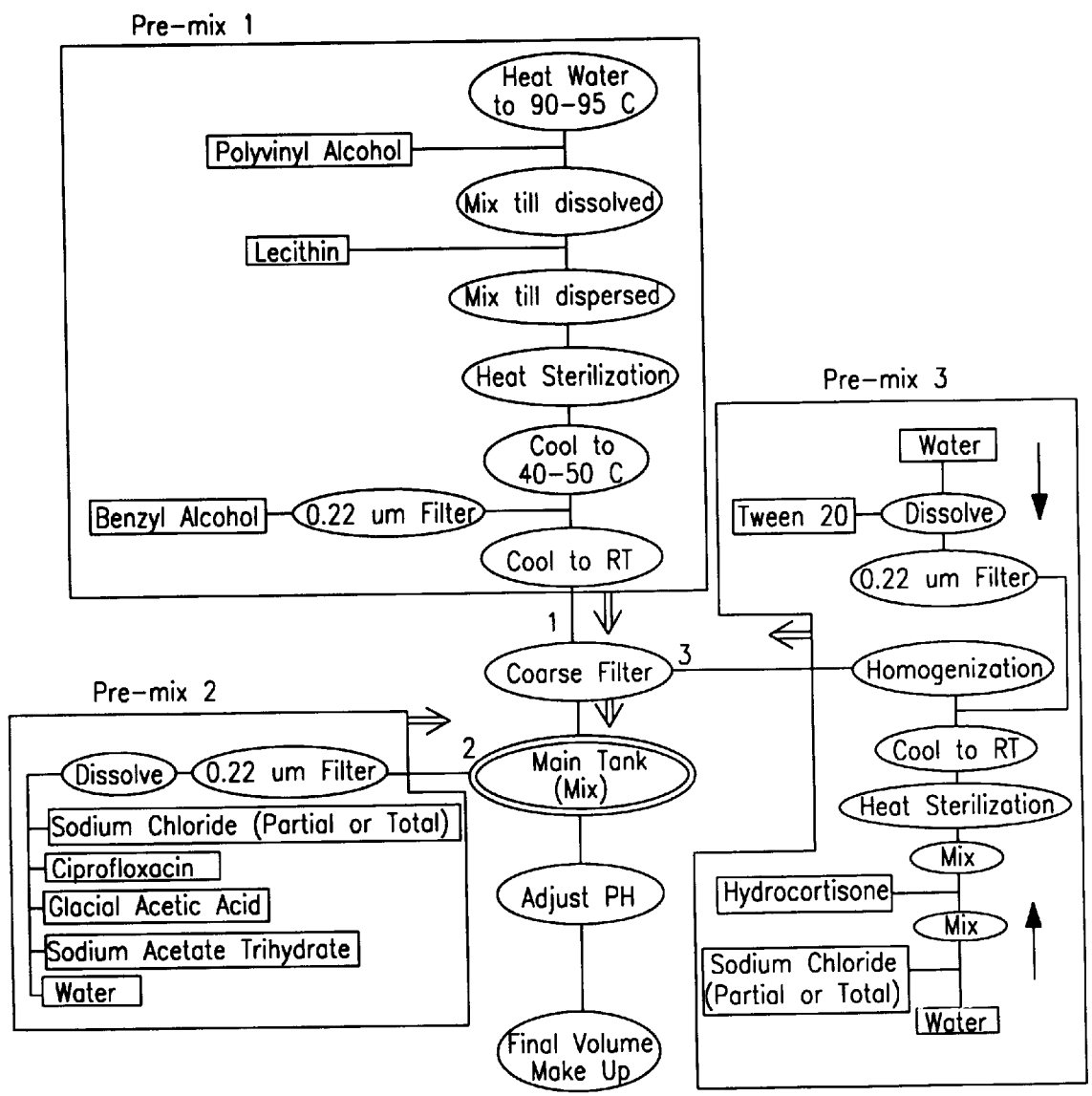
FIG. 1 is a flow-chart of one embodiment of the sterilization process.

A process is described herein to prepare sterile pharmaceutical suspensions by using a wet heat process in conjunction with aseptic technique. The process, with two variations, has been shown in two separate flowcharts, FIGS. 1 and 2, for the same formulation. The variation in each chart demonstrates the flexibility of the process in choosing any salt (such as sodium chloride, sodium acetate or any other electrolyte present in the formulation) for the purpose of sterilization of the suspended water-insoluble active ingredient (in this case, Hydrocortisone). This is in contrast to the current state-of-the-art which is that one salt, sodium chloride, is required in order to keep the hydrocortisone out of solution at the higher temperatures of the wet steam method. In addition, it is surprising that less than a saturated solution of sodium chloride could be used during wet steam sterilization of the corticosteroid, because as discussed in U.S. Pat. No. 3,962,430 (O'Neil) in col. 2, lines 27–33, the current thought is that it is required to have the solution saturated.

Briefly, the invention is a method for sterilizing a pharmaceutical formulation comprising a suspension of a water-insoluble pharmaceutical such as a corticosteroid, comprising the steps of first heat-sterilizing water, PVA and Lecithin. Wet heat is preferred, at a temperature of 121 degrees centigrade. This is followed by aseptic addition of benzyl alcohol to the heat sterilized aqueous mixture of PVA and lecithin to give a first sterile pre-mix. "Aseptic addition" may be attained by filtering through 0.22 micron filters, and by maintaining the mixing equipment sterile by well-known aseptic methods.

The second sterile pre-mix is made by filtering under sterile conditions a mixture of water, a pharmaceutically active compound, acetic acid, and a partial amount of an electrolyte to give a second sterile pre-mix. "Pharmaceutically active compounds" are chemicals that interact with a biological system such that some beneficial thereapeutic effect is made on the biological system. Many such compounds are known, and are listed in the Physician's Desk Reference, Remington's Pharmaceutical Sciences, or the Merck Index. In particular, the quinolone anti-infective Ciprofloxacin® (Bayer Corporation, Pharmaceutical Division, West Haven, Conn.) is demonstrated herein. Any pharmaceutically active compound or that may be formulated as a suspension comes within the scope of this invention.

A third pre-mix is then made by heat-sterilizing a mixture of water, a micronized corticosteroid, and at least a partial (or full) amount of the electrolyte using less than a saturated solution of the electrolyte, and adding under aseptic conditions water and Tween 20, to give a third sterile pre-mix. A "micronized" corticosteroid or water-insoluble pharmaceutical means a dry particulate water-insoluble pharmaceutical having 98% of the particles $\leq 5\mu m$, and 100% of the particles $\leq 15\mu m$. "Electrolyte" as used herein means an electrolyte selected from the group consisting of sodium chloride; sodium acetate; potassium acetate; sodium or potassium monobasic, dibasic or tribasic phosphate; sodium or potassium citrate; sodium or potassium tartrate; sodium benzoate; sodium or potassium sorbate; sodium or potassium phthalate; sodium or potassium metabisulphite; or other similar salts usually used in a pharmaceutical suspension product.

The flexibility of the process lies in optimizing the resuspendability of the suspension by balancing one or more electrolyte amounts between the second and third sterile pre-mixes so that the total amount of the electrolyte(s) in the overall formulation remains the same.

Last, the sterile suspension is finalized by combining all three pre-mixes in sterile fashion to achieve a sterile suspended pharmaceutical formulation.

The invention is best described in conjunction with the schematic shown in FIG. 1. FIG. 1 is a schematic which is comprised of three separate sub-trees showing three corresponding sub-processes depicted as pre-mix 1, pre-mix 2 and pre-mix 3. Overall, the three pre-mixes are independently created and then combined under aseptic conditions to give a sterile suspension product having the positive resuspendability attributes claimed. Two of the pre-mixes are sterilized by wet heat, and the third one, a solution, is sterilized by aseptic filtration.

Figure 2:
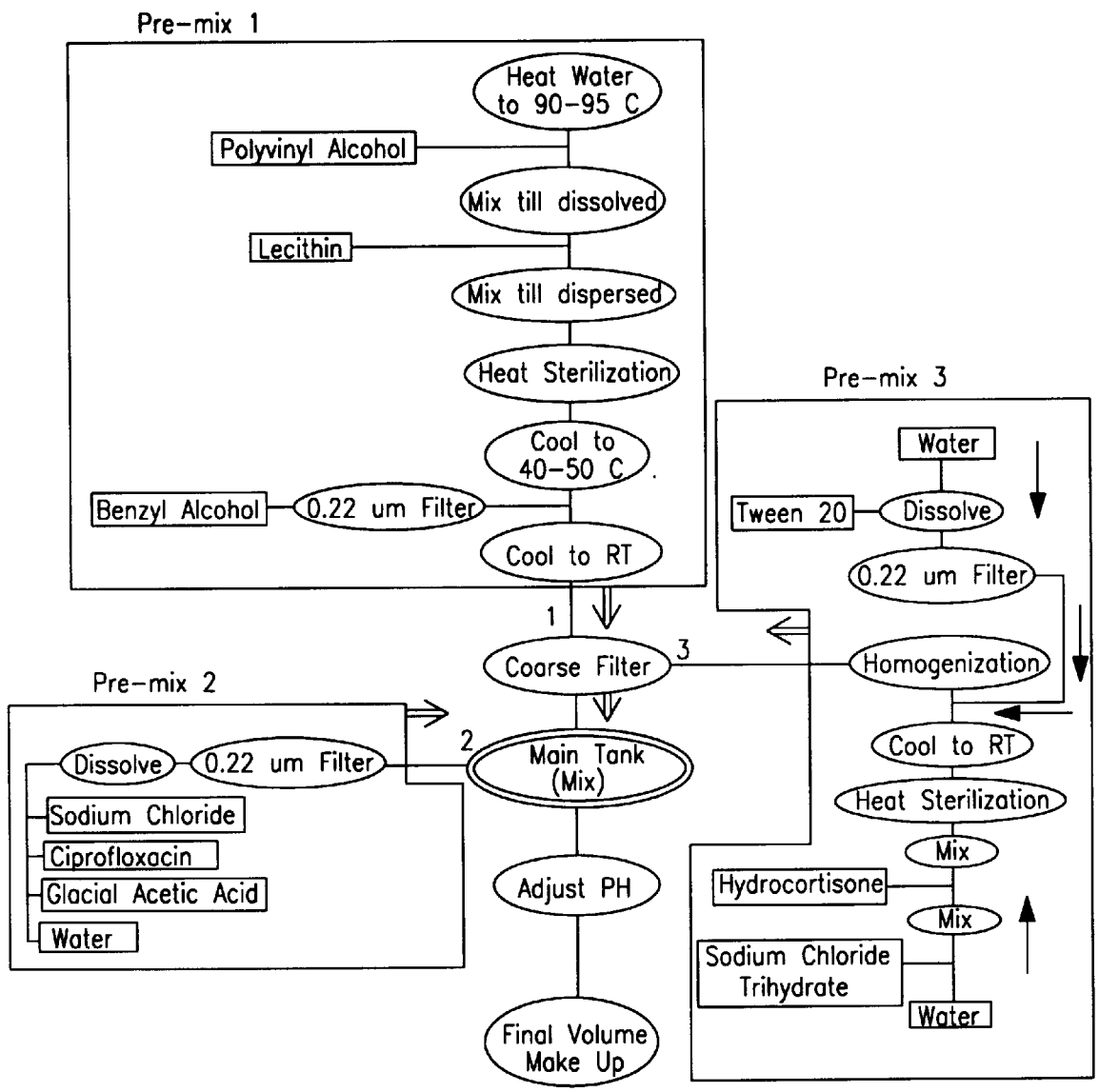
FIG. 2 is a flow-chart of another embodiment of the sterilization process, this process differing in that pre-mix 3 uses sodium acetate, and pre-mix 2 uses all of the total formulation's sodium chloride.

FIGS. 1 and 2 vary only in the type and amounts of electrolytes used in pre-mixes 2 and 3. For example, in FIG. 1. Sodium chloride (NaCl) is the selected electrolyte and the total amount of NaCl is split between pre-mix 2 and pre-mix 3. However, other electrolytes may be used, and may be substituted in whole by sodium acetate (NaAc), as shown in the pre-mix 3 section of FIG. 2, or in part. The only critical factor is that the electrolytes must be selected and balanced between pre-mix 2 and 3 so that optimum suspension characteristics are maintained. "Optimum suspension characteristics" means the most sediment volume measured indirectly through flocculation height (mm), and resuspendability in terms of the least number of strokes needed to re-disperse the flocculate. Redispersability is one of the major considerations in assessing the acceptability of a suspension. The sediment formed due to sitting should be easily re-dispersed by moderate shaking to yield a homogenous system. Measurement of the sedimentation volume and its ease of redispersion form two of the most basic evaluative procedures according to the text *Theory and Practice of Industrial Pharmacy*, L. Lachman et al., 2d Ed., pp 159, 180. The methods suggested in this text were adapted to assess resuspendability and sedimentation rate of candidate compositions and to discover materials enhancing the suspension of hydrocortisone in an aqueous base. Resuspendability of candidate compositions was assessed by the number of inversions, termed "strokes", required to redisperse sedimentation which was visible in a stoppered cylinder containing a specimen of a composition after standing undisturbed overnight. Sedimentation rate was assessed by observing the height in millimeters of the column of sedimentation visible in 20 millimeters of specimen suspension contained in a cylinder after shaking and then standing overnight. Larger heights were favorable indicating less separation with less supernatant liquid and less compaction of sedimentation.

Figure 3:
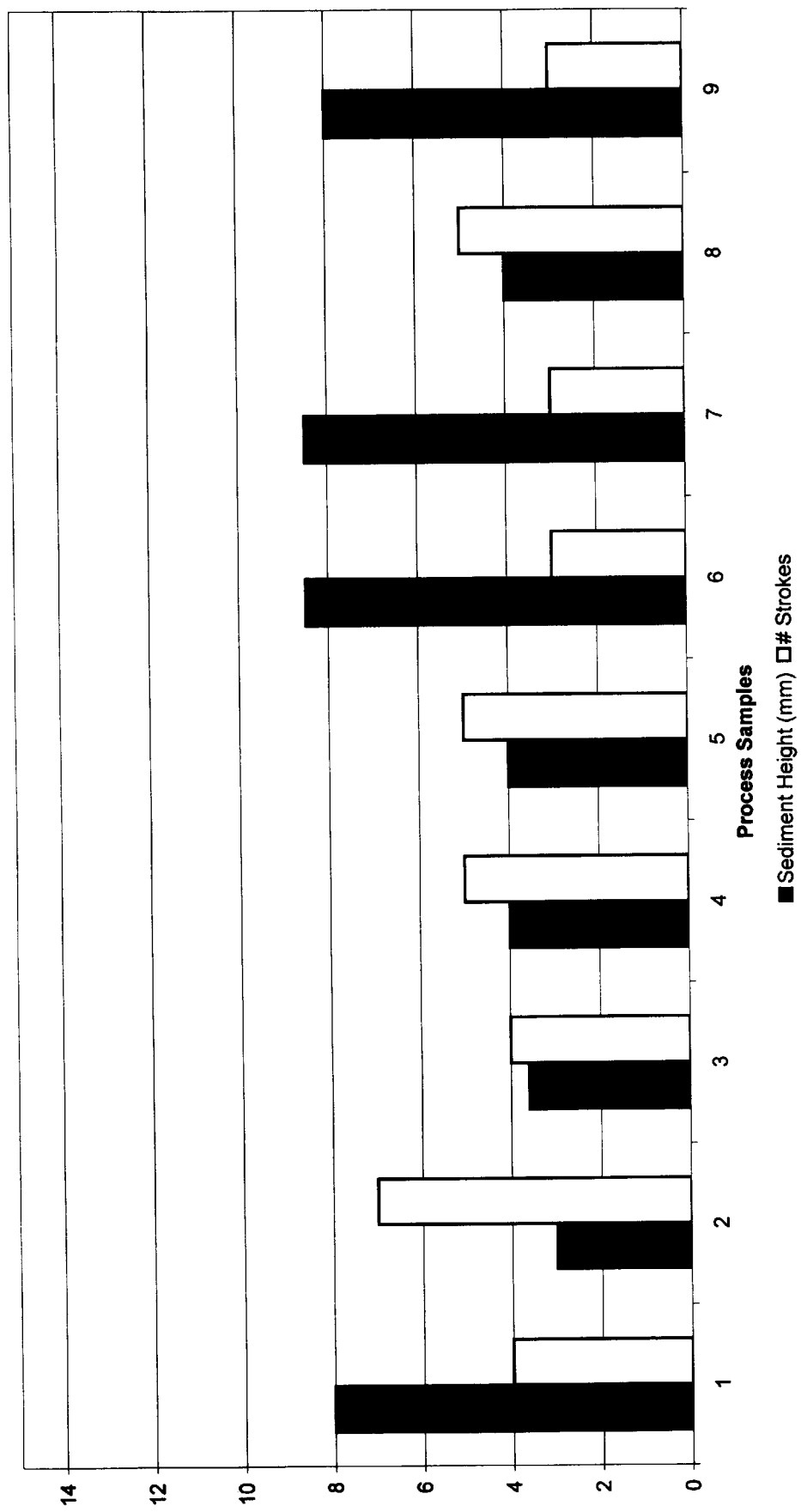
FIG. 3 is a histogram illustrating the autoclaving effect on the various suspensions, depicting flocculation height in millimeters, and number of strokes to re-disperse the flocculate after sitting for 24 hours.

FIG. 3 is a histogram showing three parameters: the amount of flocculate height after 24 hours (mm), and the number of strokes to re-disperse the flocculate uniformly after 24 hours (note: the terms "re-suspend" and "re-disperse" are used interchangeably throughout). The horizontal axis depicts the experimental sample number (which corresponds to a specific electrolyte balance between pre-mixes 2 and 3), and the vertical axis depicts either the height of the flocculate in millimeters, or the absolute number of strokes to re-suspend the flocculate, depending upon which of the three bars one is reading. For example, Process Sample 1 is the control-no sterilization step was performed on it. It represents the optimum case scenario in terms of re-suspendability. The height of its sediment was about 8 mm, and it took only 4 strokes to re-suspend after 24 hours of sitting. In contrast, adding electrolyte at less than a saturated amount and sterilizing the composition resulted in lower sediment heights (see sample #s 3–5, and 8) and almost same number of strokes (from 4 to 5) to re-disperse. However, the scale-up batches (Samples 6 and 7) for the process sample 5 were very similar to Control process sample 1. Process Sample 9 is a formulation having sodium acetate only as the electrolyte, which has characteristics that are approximately the same as the Control (8 mm sediment height, 3 strokes to re-suspend). Overall, there is not much variability between the different formulations, demonstrating that they all behave similarly, which is the goal. In contrast, a formulation having 0% NaCl (process sample 2) was made for the purpose of comparison, and after sterilization it required most number of strokes (7) to redisperse. Table 1 lists the samples:

TABLE 1

| Process Sample | Description |
| --- | --- |
| 1 | Non-sterilized Product Batch (control) |
| 2 | 0% NaCl in HC pre-mix |
| 3 | 0.3% NaCl in HC pre-mix |
| 4 | 0.45% NaCl in HC pre-mix |
| 5 | 0.6% NaCl in HC pre-mix scale-up |
| 6 | 0.6% NaCl, scale-up batch 1 (30 liters) |
| 7 | 0.6% NaCl, Production batch 2 (30 liters) |
| 8 | 0.9% NaCl in HC pre-mix |
| 9 | 0.68% NaAc |

Preparation of Pre-mix 1

Pre-mix 1 is depicted in the top portion of FIG. 1. For the 1st pre-mix, polyvinyl alcohol (PVA) (Airvol™ 125, Air Products Inc.; 99% hydrolyzed preferred) was dissolved in approx. 40–45% of the water required for the batch by heating at 90–95° C. After the PVA was dissolved, Lecithin (Phospholipon 90H; vendor: American Lecithin) was dispersed, followed by sterilization of the mixture by wet heat. The PVA-water-Lecithin mixture was then cooled to around 40–50° C. at which point benzyl alcohol was added aseptically using 0.22 μm sterilizing filter (Millipore Corp., Bedford, Mass.) and stirred to mix. The PVA-water-Lecithin-benzyl alcohol mixture was cooled to room temperature and then held until final assembly.

Preparation of Pre-mix 2

Soluble components such as sodium chloride (full or partial quantity as the case may be), sodium acetate, glacial acetic acid, Ciprofloxacin® HCl etc. can be dissolved in this pre-mix using approximately 30% of the water required for the entire batch. For example, if the batch size is always 100 kg, then up to 30 kg (30 liters) may be water.

With particular attention again to FIG. 1, 0.3% of the sodium chloride of the total was used in pre-mix 2, while the remaining 0.6% is used in the pre-mix 3. This ratio represents a particularly preferred ratio and has been discovered to be the optimum re-suspension ratio.

Alternately, for the process as shown in flow chart 2, the entire quantity of sodium chloride could be used in pre-mix 2, and for pre-mix 3 all of sodium acetate could be used (for optimum suspension characteristics). After all the components are dissolved, the premix is held until final assembly.

Preparation of Pre-mix 3

The partial quantity of sodium chloride (for the process in flow chart 1) or the entire quantity of sodium acetate (for the process in flow chart 2) was dissolved in enough quantity of water such that after hydrocortisone was added to this premix, the pre-mix weight should be approximately 3.5% of the batch size (for example, for a 100 kg batch, the total weight of this pre-mix prior to autoclaving should be no more than 3.5 kg consisting of water, electrolyte, and hydrocortisone) This requirement is for obtaining optimum suspension characteristics, however, for less than optimum characteristics, this value could be varied from 2.5 to 5.0%.

Starting at the bottom of the pre-mix 3 schematic and working up to the homogenization point, after the electrolyte (salt) was dissolved, hydrocortisone was added to it and it was shaken/mixed to adequately wet it (using less water may cause hindrance in wetting process). The pre-mix was sterilized by wet heat.

Other water-insoluble pharmaceuticals such as a corticosteroid may be used as well, such as for example cortisone and its esters, cortisolone and its esters, dexamethasone and its esters, hydrocortisone and its esters, prednisolone and its esters, prednisone and its esters, fluocinolone and its esters, triamcinolone and its esters, and other corticosteroids. Further, other water-insoluble pharaceutically active compounds may also be used. The term "water-insoluble pharmaceutical" is used herein to encompass corticosteroids and other insoluble pharmaceuticals that may be used as the suspended components in a suspension. Any water-insoluble pharmaceutically active compound that may be formulated as a suspension comes within the scope of this invention.

Working down from the top of the pre-mix 3 schematic, Tween™ 20 (Polysorbate 20) was dissolved in approximately 6.5% water of the batch by weight and added aseptically to the sterilized hydrocortisone-salt mixture by passing it through a 0.22 $\mu$m filter (total pre-mix weight at this point is approximately 10% of the batch size).

The hydrocortisone/salt mixture and the Tween solution were mixed and then homogenized under aseptic condition using a homogenizer at 2000 rpm for 10 minutes (Model L4R, Silverson, E. Longmeadow, Mass.). The pre-mix is then held under sterile conditions until final assembly.

Assembly of the Final Product

Pre-mix 1 was mixed and transferred aseptically using a coarse filter into the main tank. Mixing was started and pre-mix 2 was added aseptically into the main tank, filtering it through a 0.22 $\mu$m filter while continuing to mix. Pre-mix 3 was transferred aseptically to the main tank using a course filter while continuing to mix the tank's contents.

The total volume was made up aseptically to 97% of the batch size using water and passing it through a 0.22 $\mu$m filter. Mixing continued and the pH was checked and adjusted if necessary to the desired level, pH 4.2–5.2, or more preferably pH 4.5–4.7. The volume was made up to 100% of batch. The final suspension was mixed and stored until ready for filling and packaging.

EXAMPLES

Example 1

Cipro-Hydrocortisone Otic Suspension having 0.3% NaCl in pre-mix 2 (Cipro), and 0.6% NaCl in pre-mix 3 (hydrocortisone).

A sterile Ciprofloxacin-hydrocortisone suspension having the following formula was made according to the previously-described method shown in FIG. 1:

| | | |
|---|---|---|
| 1. Ciprofloxacin HCl, USP/NF/EP | 0.2329 | g |
| 2. Hydrocortisone (USP, NF/EP, micronized) | 1.00 | |
| 3. Benzyl alcohol (USP/NF/EP) | 0.90 | |
| 4. PVA (Airvol 125) | 2.00 | g |
| 5. Sodium Chloride, USP/NF/EP | 0.90 | |
| 6. Lecithin (Phospholipon 90H) | 0.15 | |
| 7. Tween 20 Polysorbate 20), USP/NF/EP | 0.10 | |
| 8. Glacial acetic acid, USP/NF/EP | 0.255 | |
| 9. Sodium acetate, trihydrate, USP/NF/EP | 0.68 | |
| 10. Purified water, USP/NF/EP, q.s. to | 100.0 | ml |
| | (101.5 | g) |

This formulation has been shown to be effective as an antibiotic for treatment of otitis externa as shown in co-pending U.S. patent application Ser. Nos. 08/465,048; 709,245; and 838,473, incorporated herein by reference.

The re-suspendability of this batch is shown in FIG. 3 in process sample #5. It took 5 strokes to re-disperse the flocculate, as compared to 4 strokes to re-disperse the control sample # 1. There was no substantial caking over time. However, the same experiment when scaled up to a 30 liter batch in duplicate, the sediment height of 8.5 mm and 3 strokes to re-dispesre, shown as Examples 6 and 7 in FIG. 3, were very similar to Control sample 1.

Example 2

Cipro-Hydrocortisone Otic Suspension having 0.9% NaCl in pre-mix 2, and 0% NaCl in pre-mix 3 (hydrocortisone).

The same formulation as shown in Example 1 was used, however the electrolyte (NaCl) was all in the Ciprofloxacin pre-mix and the effect on re-suspendability was analyzed. Sample 2 shows that the flocculate height (3 mm) was less than half of the control's height (8 mm), and it took more strokes (7) to re-disperse than the control (4). Clearly, there is some need to have electrolyte present with the hydrocortisone.

Example 3

Cipro-Hydrocortisone Otic Suspensions having 0.6%, 0.45% and 0% NaCl in pre-mix 2, and 0.3%, 0.45% and 0.9% NaCl in pre-mix 3, respectively.

Again the same formulation as shown in Example 1 was used, the electrolyte (NaCl) was split between the two pre-mixes, and the effect on re-suspendability was analyzed.

The re-suspendability of these three batches is shown in FIG. 3 in process sample numbers 3, 4 and 8, respectively. For all three, it took 4 or 5 strokes to re-disperse the flocculate, as compared to 4 strokes to re-disperse the control sample. There was no substantial caking over time. Also, flocculate heights were remarkably similar at about 4 mm. These three examples were very similar to Example 1, which is represented in FIG. 3 as Sample 5.

Example 4

Cipro-Hydrocortisone Otic Suspension having all of NaAcetate (0.68%) in pre-mix 3, while all of Sodium Chloride in pre-mix 2.

Using the formulation of Example 1, the process of FIG. 2 was used.

The re-suspendability of this batch is shown in FIG. 3 in process sample #9. It took only 3 strokes to re-disperse the flocculate, as compared to 4 strokes to re-disperse the control sample. There was no substantial caking over time. The flocculate height was the same as the NaCl control (sample 1).

Figure 4:
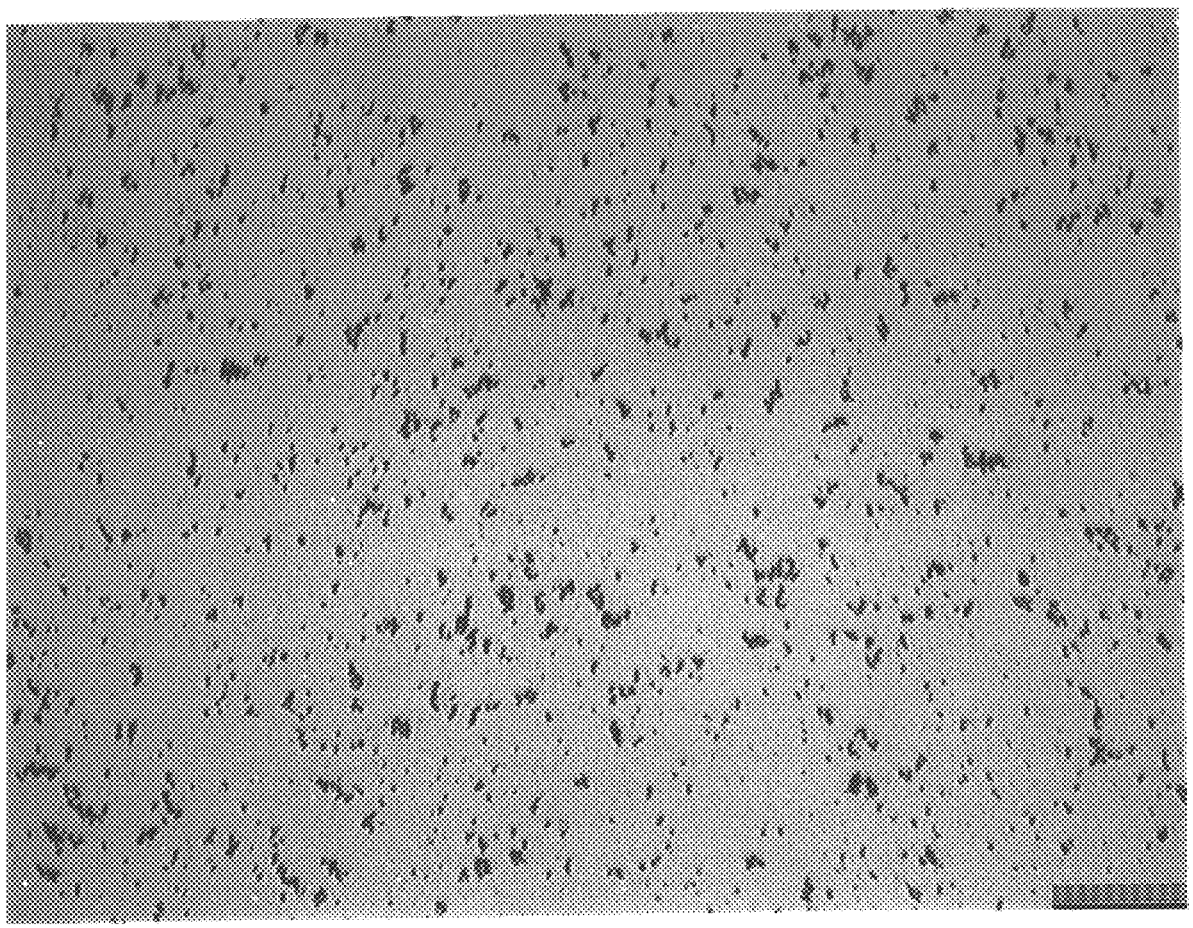
FIG. 4 is a photomicrograph (100×) of a suspension of CiproHC™ Otic suspension, unsterilized.
Figure 5:
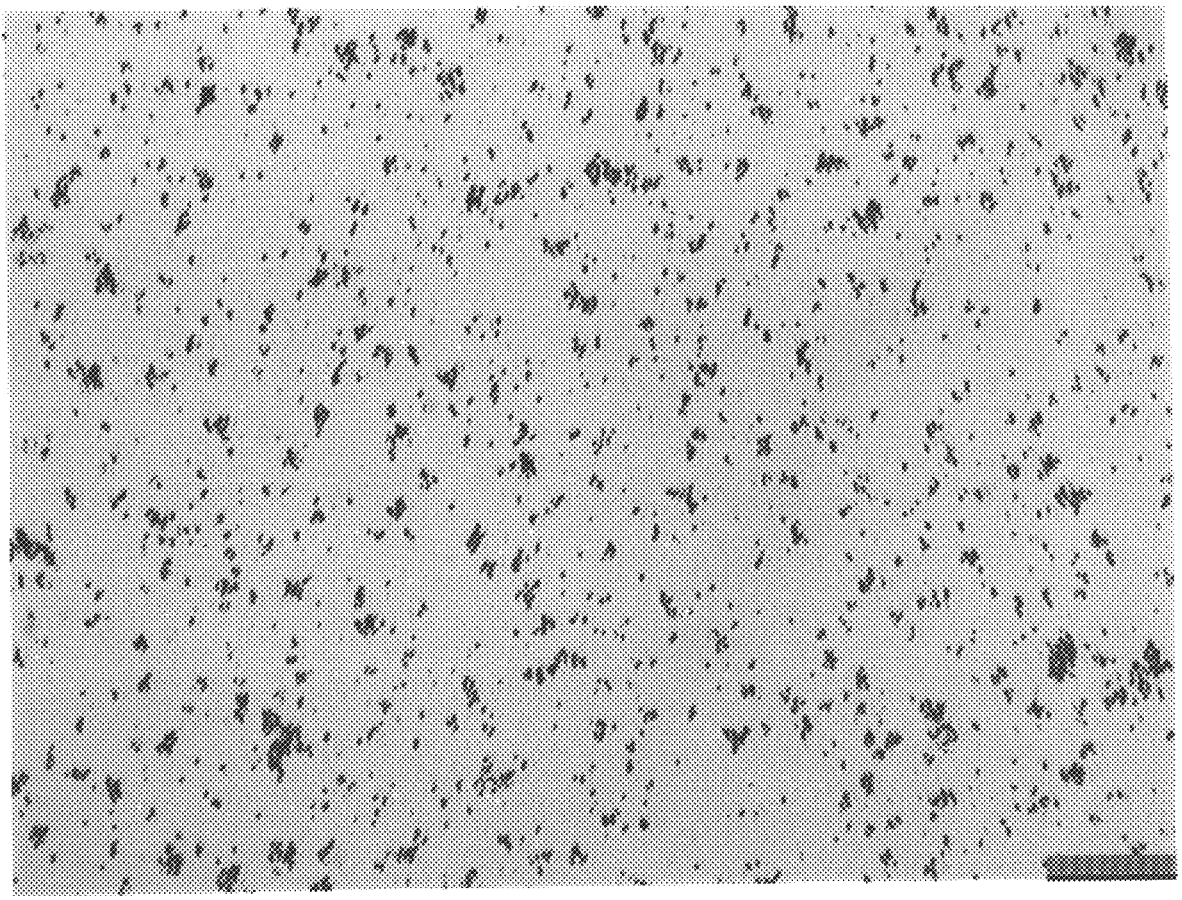
FIG. 5 is a photomicrograph (100×) of a suspension of CiproHC™ Otic suspension, sterilized according to this invention, with pre-mix 3 having 0.6% NaCl.

FIGS. 4–5 are photomicrographs of the non-sterilized CiproHC Otic suspension (FIG. 4), and the sterilized suspension (FIG. 5). Note that both are very similar in regards to the primary particles' sizes.

Examples 5–8

Effect of the use of Other Corticosteroids on the Suspension Sterilization Process.

Figure 6:
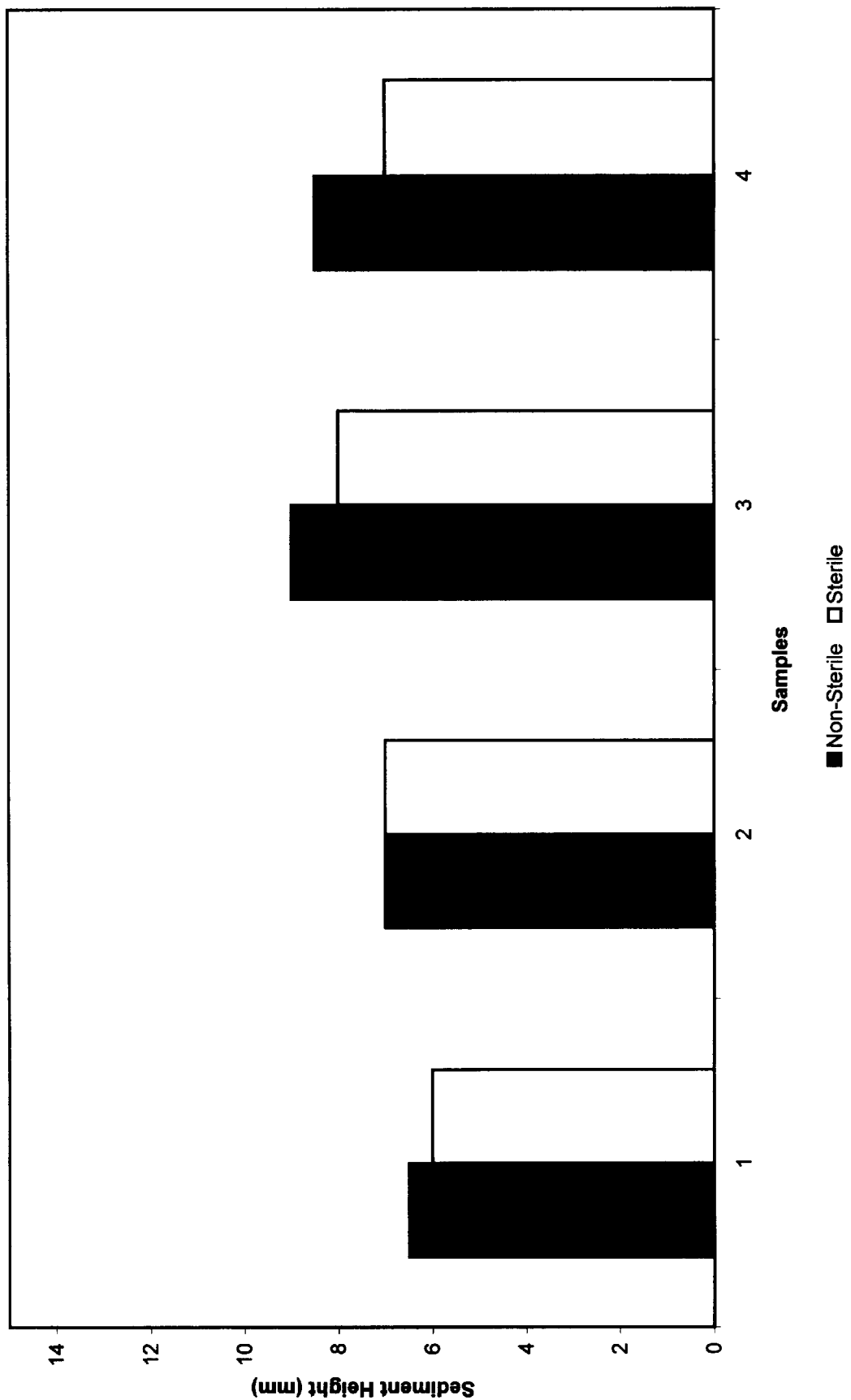
FIG. 6 is a histogram depicting the effect of the sterilization process on sediment height (mm) of 4 samples of different corticosteroids: Sample 1 is Hydrocortisone acetate; Sample 2 is Dexamethasone; Sample 3 is Dexamethasone acetate; and Sample 4 is Prednisone.
Figure 7:
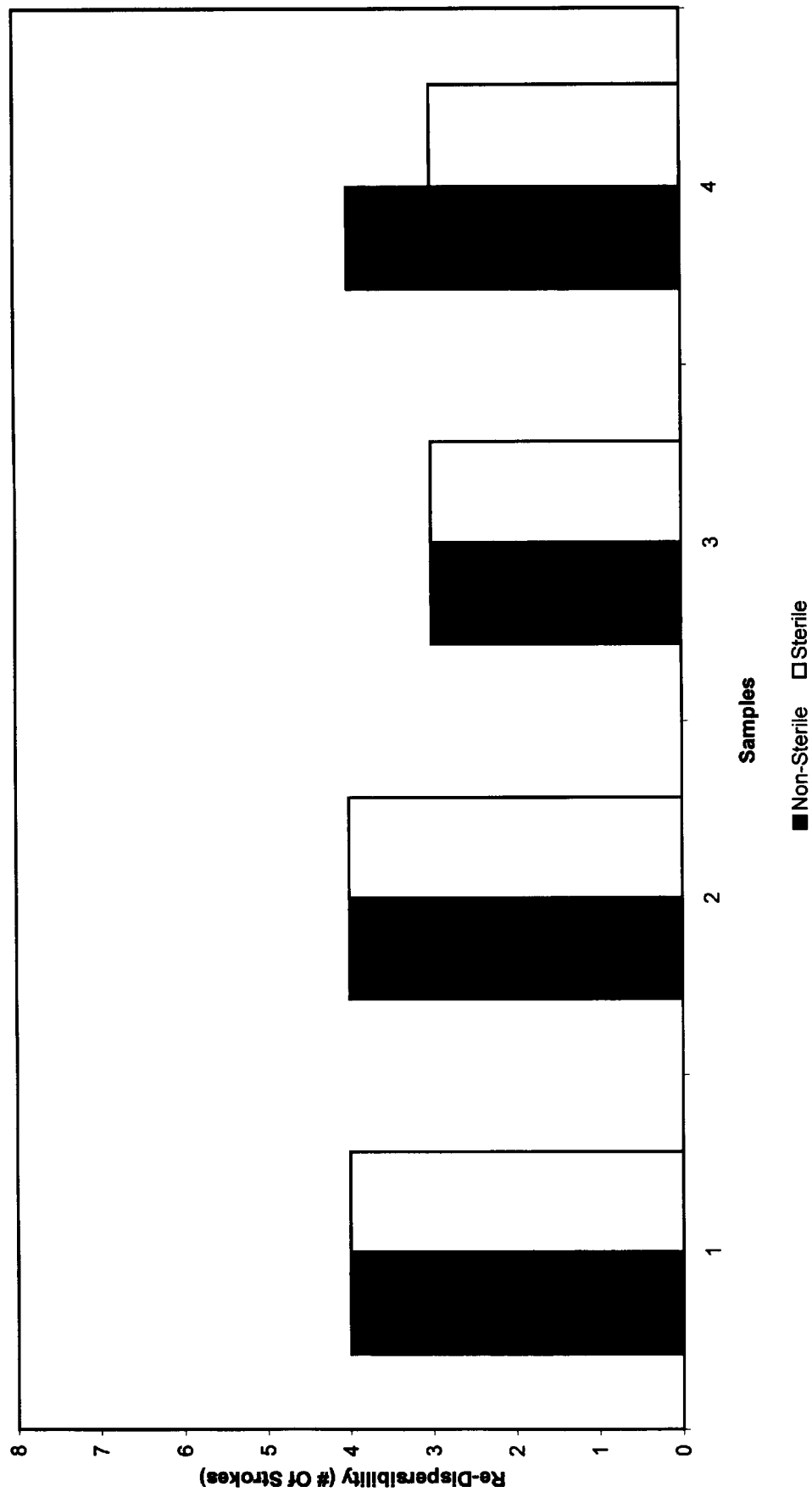
FIG. 7 is a histogram showing re-dispersability of Samples 1–4 from FIG. 6, characterized by stroke number to re-disperse.

Examples 5–8 show Hydrocortisone acetate, Dexamethasone, Dexamethasone acetate, and Prednisone, respectively, used in place of Hydrocortisone in the formulation of Example 1. FIG. 6 is a histogram depicting the effect of the sterilization process on sediment height (mm) of the 4 samples of the different corticosteroids: Sample 1 is Hydrocortisone acetate; Sample 2 is Dexamethasone; Sample 3 is Dexamethasone acetate; and Sample 4 is Prednisone. The sediment height for all four samples are very similar for the sterilezed versus the non-sterilied samples, and so were the the re-dispersability, as seen in the almost uniformly identical stroke numbers in FIG. 7.

FIGS. 8–11 show the photomicrographs (100×) of non-sterile (top) and sterilized (bottom) suspension samples. FIG. 8 is Hydrocortisone acetate; FIG. 9 is Dexamethasone; FIG. 10 is Dexamethasone acetate; FIG. 11 is Prednisone. These photos confirm the data shown in FIGS. 6 and 7, in that the sterilization process does not significantly cause re-crystallization or change in the primary particle size of the corticosteroids.

From the foregoing it will be appreciated that, although specific embodiments of the invention have been described herein for purposes of illustration, various modifications may be made without deviating from the spirit and scope of the invention and the following claims. As examples, the steps of the preferred embodiments constitute only one form of carrying out the process in which the invention may be embodied. For instance, using the teachings contained herein one of skill in the art may be able to test and thereby select other combinations of electrolytes for use in pre-mixes 2 and 3 by optimizing the combination of a high flocculate reading combined with a low number of strokes for redispersion. These new combinations would be within the spirit and scope of this invention.

I claim:

1. A method for sterilizing a pharmaceutical suspension of a water-insoluble pharmaceutical, comprising the steps of:
   (a) heat-sterilizing an aqueous solution of a viscosity enhancer, to result in a first sterile pre-mix;
   (b) sterile-filtering an aqueous solution of a mixture of a pharmaceutically-active compound, which results in a second sterile pre-mix;
   (c) heat-sterilizing a mixture of water, a water-insoluble pharmaceutical, and at least a partial amount of an electrolyte to provide a sub-saturated solution of said electrolyte, and adding under aseptic conditions an aqueous surfactant, to give a third sterile pre-mix;
   (d) combining all three pre-mixes in sterile fashion to achieve a sterile suspended pharmaceutical formulation.

2. The method of claim 1 wherein said viscosity enhancer is polyvinyl alcohol or lecithin.

3. The method of claim 2 wherein said polyvinyl alcohol is at least 85% hydrolyzed.

4. The method of claim 1 wherein said electrolyte is selected from the group consisting of sodium chloride; sodium acetate; potassium acetate; sodium or potassium monobasic, dibasic or tribasic phosphate; sodium or potassium citrate; sodium or potassium tartrate; sodium benzoate; sodium or potassium sorbate; sodium or potassium phthalate; sodium or potassium and or other similar electrolytes used in a pharmaceutical suspension product.

5. The method of claim 1 wherein said electrolyte is sodium chloride or sodium acetate.

6. The method of claim 1 wherein said water-insoluble pharmaceutical is selected from the group consisting of cortisone, cortisolone, dexamethasone, hydrocortisone, prednisolone, prednisone, fluocinolone, triamcinolone, and their pharmaceutically-compatible esters.

7. The method of claim 1 wherein the first sterile pre-mix contains in addition a preservative.

8. The method of claim 7 wherein said preservative is benzyl alcohol.

9. The method of claim 1 wherein said pharmaceutically active compound is Ciprofloxacin.

10. The method of claim 1 wherein said water-insoluble pharmaceutical is Hydrocortisone.

11. The method of claim 1 wherein a pharmaceutically compatible acid, base or buffer in sufficient amount to result in a pH that enables solubilization of said pharmaceutically active compound is optionally included.

12. A method for sterilizing a pharmaceutical suspension of a water-insoluble pharmaceutical, comprising the steps of:
   (a) heat-sterilizing an aqueous solution of a viscosity enhancer, to give a first sterile pre-mix;
   (b) sterile-filtering an aqueous solution of a pharmaceutically-active compound, and at least a partial amount of an electrolyte to give a second sterile pre-mix;
   (c) heat-sterilizing a mixture of water, a water-insoluble pharmaceutical, and at least a partial amount of said electrolyte using less than a saturated solution of said electrolyte, and adding under aseptic conditions an aqueous surfactant, to give a third sterile pre-mix;
   (d) optimizing resuspendability of the suspension by balancing the amounts of electrolyte between said second and third sterile pre-mixes so that the total amount of said electrolyte is the total formula amount of the batch formulation; and
   (e) combining all three pre-mixes in sterile fashion thereby achieving a sterile suspended pharmaceutical formulation.

13. The method of claim 12 wherein said viscosity enhancer is polyvinyl alcohol or lecithin.

14. The method of claim 13 wherein said polyvinyl alcohol is at least 85% hydrolyzed.

15. The method of claim 12 wherein said electrolyte is selected from the group consisting of sodium chloride; sodium acetate; potassium acetate; sodium or potassium monobasic, dibasic or tribasic phosphate; sodium or potassium citrate; sodium or potassium tartrate; sodium benzoate; sodium or potassium sorbate; sodium or potassium phthalate; sodium or potassium metabisulphite; and other similar electrolytes used in a pharmaceutical suspension product.

16. The method of claim 12 wherein said electrolyte is sodium chloride or sodium acetate.

17. The method of claim 12 wherein said water-insoluble pharmaceutical is selected from the group consisting of cortisone, cortisolone, dexamethasone, hydrocortisone, prednisolone, prednisone, fluocinolone, triamcinolone, and their pharmaceutically-compatible esters.

18. The method of claim 12 wherein the first sterile pre-mix contains in addition a preservative.

19. The method of claim 18 wherein said preservative is benzyl alcohol.

20. The method of claim 12 wherein said electrolyte is sodium chloride, the total amount of which is divided between pre-mix 2 and pre-mix 3.

21. The method of claim 20 wherein said division is from about 0% of the total formula amount to less than the saturation concentration of said electrolyte.

22. The method of claim 20 wherein said division is about 0.3% in pre-mix 2, and about 0.6% in pre-mix 3.

23. The method of claim 12 wherein said electrolyte other than sodium chloride in pre-mix 3 could be in any concentration from saturated to less than saturated.

24. The method of claim 12 wherein said balancing requires minimizing the amount of water in said third sterile pre-mix.

25. The method of claim 12 wherein said pharmaceutically active compound is Ciprofloxacin.

26. The method of claim 12 wherein said water-insoluble pharmaceutical is Hydrocortisone.

27. The method of claim 12 wherein a pharmaceutically compatible acid, base or buffer in sufficient amount to result in a pH that enables solubilization of said pharmaceutically active compound is optionally included.

28. A pharmaceutical suspension made according to the method of claim 1.

29. A pharmaceutical suspension made according to the method of claim 12.

30. The method of claim 11 wherein said pharmaceutically compatible acid is selected from the group consisting of acetic acid, hydrochloric acid, sulfuric, and other pharmaceutically compatible acids.

* * * * *